United States Patent [19]

Christensen et al.

[11] Patent Number: 4,729,993
[45] Date of Patent: Mar. 8, 1988

[54] CARBAPENEMS AND 1-METHYLCARBAPENEMS HAVING AN EXTERNALLY ALKYLATED MONO- OR BICYCLIC 2-QUATERNARY HETEROARYLALKYL SUBSTITUENT

[75] Inventors: Burton G. Christensen, Cliffside; Ronald W. Ratcliffe, Matawan; James V. Heck, Fanwood; Thomas N. Salzmann, North Plainfield; David H. Shih, Manalapan, all of N.J.

[73] Assignee: Merck & Co., Inc., Rahway, N.J.

[21] Appl. No.: 681,179

[22] Filed: Dec. 13, 1984

[51] Int. Cl.$^4$ .................. C07D 499/00; A61K 31/425
[52] U.S. Cl. .................... 514/210; 540/350; 540/302
[58] Field of Search ............. 260/245.2 T, 245.2 R; 514/210; 540/350, 310, 302, 210

[56] References Cited

U.S. PATENT DOCUMENTS

| | | | |
|---|---|---|---|
| 4,189,493 | 2/1980 | Christensen et al. | 424/273 R |
| 4,218,459 | 8/1980 | Cama et al. | 424/270 |
| 4,260,627 | 4/1981 | Christensen et al. | 424/274 |
| 4,262,009 | 4/1981 | Christensen et al. | 424/274 |
| 4,262,011 | 4/1981 | Christensen et al. | 424/274 |
| 4,312,871 | 1/1982 | Christensen et al. | 424/263 |
| 4,341,706 | 7/1982 | Christensen et al. | 260/245.2 T |
| 4,347,355 | 8/1982 | Chu | 542/350 |
| 4,348,320 | 9/1982 | Bouffard et al. | 260/239 |
| 4,377,591 | 3/1983 | Hiraoka et al. | 424/274 |
| 4,465,632 | 8/1984 | Christensen et al. | 260/245.2 T |
| 4,536,335 | 8/1985 | Kim et al. | 260/245.2 R |
| 4,680,292 | 2/1987 | Christensen et al. | 514/210 |

FOREIGN PATENT DOCUMENTS

| | | |
|---|---|---|
| 56-60852 | 10/1982 | Japan . |
| 56-199682 | 6/1983 | Japan . |
| 57-145086 | 2/1984 | Japan . |
| 57-145087 | 2/1984 | Japan . |
| 2092147A | 8/1982 | United Kingdom . |
| 2119371A | 11/1983 | United Kingdom . |
| 2122196A | 1/1984 | United Kingdom . |
| 2128187A | 4/1984 | United Kingdom . |

Primary Examiner—Nicholas S. Rizzo
Attorney, Agent, or Firm—Raymond M. Speer; Robert J. North; Hesna J. Pfeiffer

[57] ABSTRACT

Carbapenems having the formula:

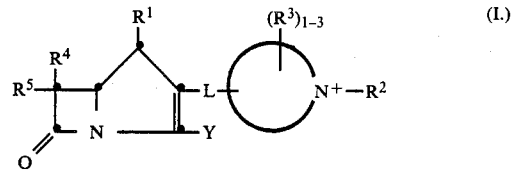

wherein

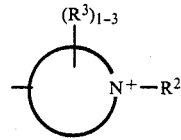

is mono- or bicyclic quaternary heteroaryl, their preparation and antibiotic use are disclosed.

21 Claims, No Drawings

CARBAPENEMS AND 1-METHYLCARBAPENEMS HAVING AN EXTERNALLY ALKYLATED MONO- OR BICYCLIC 2-QUATERNARY HETEROARYLALKYL SUBSTITUENT

BACKGROUND OF THE INVENTION

The present invention is concerned with carbapenem and 1-methylcarbapenem antibiotics having a quaternary mono- or bicyclic heteroaryl alkyl group in the 2-position.

Thienamycin is a known carbapenem, broad spectrum antibiotic of the formula:

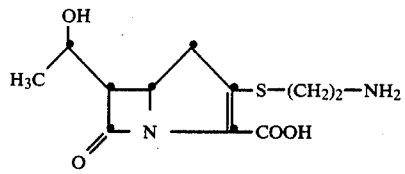

Other derivatives of A are also known.

The present externally alkylated mono- or bicyclic 2-quaternary heteroarylalkyl substituted carbapenems are believed to have an antibiotic spectrum comparable to A.

BRIEF DESCRIPTION OF DISCLOSURES IN THE ART

Sankyo U.S. Pat. No. 4,377,591 and Japanese patent publications Nos. 56-199682 and 56-60852 Shionogi Japanese patent publications Nos. 57-145086 and 57-145087; and Roche U.K. patent publication No. 2 092 147A, all describe azabicycloheptene antibiotics having a 2-position substituent joined through a thioalkylene bridge. U.S. Pat. No. 4,189,493 to Bristol-Myers discloses externally alkylated heteroarylium alkylthioazabicycloheptene antibiotics. U.S. Pat. No. 4,465,672, U.S. Pat. No. 4,260,627 and U.S. Pat. No. 4,267,188, all assigned to Merck & Co., Inc., disclose 2,6-substituted-1-carba-2-penem-3-carboxylic acids wherein the 2-substituent can be substituted or unsubstituted alkyl or aryl. However, none of the above references specifically describe the carbapenem compounds of the present invention.

SUMMARY OF THE INVENTION

Carbapenems having the formula:

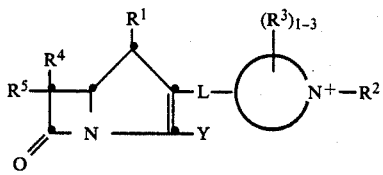

wherein $R^1$ is hydrogen or methyl; $R^2$ is a quaternizing substituent; L is an alkylene bridging group;

is mono- or bicyclic heteroarylium; and Y is a carboxy-containing substituent.

DETAILED DESCRIPTION OF THE INVENTION

The invention is embodied in a compound having the formula:

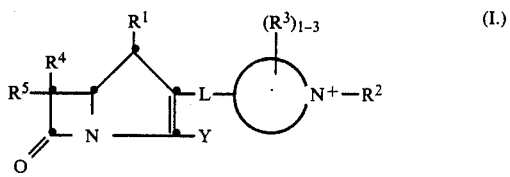

wherein:

$R^1$ is hydrogen or methyl;

$R^4$ and $R^5$ are independently H, $CH_3-$, $CH_3CH_2-$, $(CH_3)_2CH-$, $HOCH_2-$, $CH_3CH(OH)-$, $(CH_3)_2C(OH)-$, $FCH_2-$, $F_2CH-$, $F_3C-$, $CH_3CH(F)-$, $(CH_3)_2C(F)-$; $CH_3CF_2-$, or L is a bridging group comprising substituted or unsubstituted $C_1-C_4$ straight, $C_2-C_6$ branched or $C_3-C_7$ cycloalkyl groups wherein the substituents are selected from $C_1-C_6$ alkyl, $O-C_1-C_6$ alkyl, $S-C_1-C_6$ alkyl, $CF_3$, $N(C_1-C_6 \text{ alkyl})_2$;

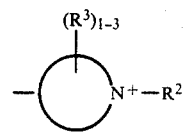

is a mono- or bicyclic heteroarylium group containing from 5-11 ring atoms of which up to 5 are heteroatoms in addition to the quaternary nitrogen;

wherein $R^2$ is (1) an unsubstituted or substituted $C_1-C_6$ alkyl radical;

(2) an unsubstituted or substituted $C_2-C_6$ alkenyl radical;

(3) an unsubstituted or substituted $C_2-C_6$ alkynyl radical;

(4) a $C_3-C_7$ cycloalkyl radical in which the ring is substituted or unsubstituted and one or more atoms may be replaced by a heteroatom;

(5) a $C_3-C_7$ cycloalkyl methyl radical in which the ring may be substituted and one or more atoms may be replaced by a heteroatom;

(6) an unsubstituted or substituted $C_5-C_7$ cycloalkenyl radical;

(7) an unsubstituted or substituted bivalent $C_2-C_6$ alkylidene radical, optionally interrupted by a heteroatom, and joined to the heteroarylium group to form a ring which is carbocyclic or in which one or more atoms is replaced by a heteroatom and wherein the new ring may contain one or more double bonds;

(8) an unsubstituted or substituted phenyl or heteroaryl radical;

(9) an unsubstituted or substituted phenyl ($C_1-C_4$ alkyl) or heteroaryl ($C_1-C_4$ alkyl) radical;

(10) a cyano ($C_1-C_4$ alkyl) radical;

(11) a carboxy ($C_1-C_4$ alkyl) radical;

(12) a sulfo ($C_1-C_4$ alkyl) radical;

(13) a carbamoyl ($C_1-C_4$ alkyl) radical;

(14) a phosphonyl ($C_1$-$C_4$ alkyl) radical;
(15) a hydroxy ($C_1$-$C_4$ alkyl) radical; or
(16) an amino ($C_1$-$C_4$ alkyl) radical in which the nitrogen atom is unsubstituted or substituted with one to three $C_1$-$C_4$ alkyl groups;

wherein the substituents in the above definitions of $R^2$ are independently selected from the group consisting of:
(a) a trifluoromethyl group;
(b) a halogen atom;
(c) an unsubstituted or substituted $C_1$-$C_4$ alkoxy radical;
(d) a hydroxy group;
(e) an unsubstituted or substituted ($C_1$-$C_6$ alkyl)carbonyloxy radical;
(f) a carbamoyloxy radical which is unsubstituted or substituted on nitrogen with one or two $C_1$-$C_4$ alkyl groups;
(g) a $C_1$-$C_6$ alkylthio radical, $C_1$-$C_6$ alkylsulfinyl radical or $C_1$-$C_6$ alkylsulfonyl radical, each of which is unsubstituted or substituted on the alkyl group;
(h) a sulfo group;
(i) a sulfamoyl group which is unsubstituted or substituted on nitrogen by one or two $C_1$-$C_4$ alkyl groups;
(j) a formylamino group;
(k) an unsubstituted or substituted ($C_1$-$C_6$ alkyl)carbonylamino radical;
(l) a ($C_1$-$C_4$ alkoxyl)carbonylamino radical;
(m) a ureido group in which the terminal nitrogen is unsubstituted or substituted with one or two $C_1$-$C_4$ alkyl groups;
(n) an arylsulfonamido or a ($C_1$-$C_6$ alkyl)sulfonamido group;
(o) a cyano group;
(p) a formyl or acetalized formyl radical;
(q) an unsubstituted or substituted ($C_1$-$C_6$alkyl)carbonyl radical wherein the carbonyl is free or acetalized;
(r) an unsubstituted or substituted phenylcarbonyl or heteroarylcarbonyl radical;
(s) a carboxyl group;
(t) a ($C_1$-$C_6$ alkoxy)carbonyl radical;
(u) a carbamoyl radical which is unsubstituted or substituted on nitrogen by one or two $C_1$-alkyl groups;
(v) an N-hydroxycarbamoyl or N($C_1$-$C_4$ alkoxy)carbamoyl radical in which the nitrogen atom may be additionally substituted by a $C_1$-$C_4$ alkyl group;
(w) a thiocarbamoyl group;
(x) a 5-(1H)-tetrazolyl group;
(y) a phosphonate group —P(O) (O⁻)OR' where R' is $C_1$-$C_3$alkyl;
(z) an alkyl phosphonate group —$(CH_2)_n$P(O) (O⁻)(OR') where n=1 to 3 and R' is $C_1$-$C_3$alkyl;
(aa) hydrogen;
(ab) an unsubstituted or substituted $C_1$-$C_6$ alkyl radical;
(ac) an unsubstituted or substituted $C_2$-$C_6$ alkenyl radical;
(ad) an unsubstituted or substituted $C_2$-$C_6$ alkynyl radical;
(ae) a $C_3$-$C_7$ cycloalkyl radical in which the ring is substituted or unsubstituted and one or more atoms may be replaced by a heteroatom;
(af) a $C_3$-$C_7$ cycloalkyl methyl radical in which the ring may be substituted and one or more atoms may be replaced by a heteroatom;
(ag) an unsubstituted or substituted $C_5$-$C_7$ cycloalkenyl radical;
(ah) an unsubstituted or substituted phenyl or heteroaryl radical; and
(ai) an unsubstituted or substituted phenyl ($C_1$-$C_4$ alkyl) or heteroaryl ($C_1$-$C_4$ alkyl) radical; and $R^3$ is
(a) hydrogen,
(b) an unsubstituted or substituted $C_1$-$C_6$ alkyl radical;
(c) an unsubstituted or substituted $C_2$-$C_6$ alkenyl radical;
(d) an unsubstituted or substituted $C_2$-$C_6$ alkynyl radical;
(e) a $C_3$-$C_7$ cycloalkyl radical in which the ring is substituted or unsubstituted and one or more atoms may be replaced by a heteroatom;
(f) a $C_3$-$C_7$ cycloalkyl methyl radical in which the ring may be substituted and one or more atoms may be replaced by a heteroatom;
(g) an unsubstituted or substituted $C_5$-$C_7$ cycloalkenyl radical;
(h) an unsubstituted or substituted phenyl or heteroaryl radical;
(i) an unsubstituted or substituted phenyl ($C_1$-$C_4$ alkyl) or heteroaryl ($C_1$-$C_4$ alkyl) radical; and
(j) a trifluoromethyl group;
(k) a halogen atom;
(l) an unsubstituted or substituted $C_1$-$C_4$ alkoxy radical;
(m) a $C_1$-$C_6$ alkylthio radical, $C_1$-$C_6$ alkylsulfinyl radical or $C_1$-$C_6$ alkylsulfonyl radical, each of which is unsubstituted or substituted on the alkyl group;
(n) a mono ($C_1$-$C_4$ alkyl) amino or di($C_1$-$C_4$ alkyl) amino group, each of which is unsubstituted or substituted on the alkyl group; or
(o) a cyano group; and Y is
(i) COOH or a pharmaceutically acceptable ester or salt thereof,
(ii) COOR wherein R is a removable carboxy protecting group, such as p-nitrobenzyl, benzyl or allyl,
(iii) COOM wheren M is an alkali metal, or
(iv) COO⁻; provided that when Y is other than (iv) a counterion Z⁻ is provided.

As used herein, the term "heteroatom" means nitrogen, oxygen, or sulfur, independently selected where more than one heteroatom is involved.

Representative L groups are substituted or unsubstituted branched or linear $C_1$-$C_4$ alkyl and include —$CH_2$—, —CH($CH_3$)—, —CH($C_2H_5$)—, —$(CH_2)_{2-4}$, —CH($CH_3$)—$CH_2$—, $CH_2$—CH($OCH_3$)—, —CH($CH_3$)—$(CH_2)_2$—, —CH($CH_2$OH)—$CH_2$—, —CH($CF_3$)—$CH_2$—, and the like.

Preferred L groups are —$CH_2$—, —CH($CH_3$)—, —$(CH_2)_2$—, and —CH($CH_3$)$CH_2$—.

Examples of useful $R^2$ groups are —$CH_3$, —$(CH_2)_{1-3}$—$CH_3$,

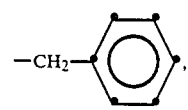

—$(CH_2)_{1-3}$—O—$CH_3$, —$CH_2$—CN, $CH_2$—$COOC_{1-C_3}$ alkyl, —$(CH_2)_2$—$N(C_1-C_3\ alkyl)_2$, —$CH_2$—COOH(Na), —$(CH_2)_2$—$SO_3H(Na)$,

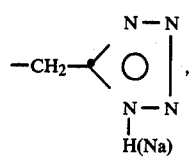

$CH_2CONH_2$, —$(CH_2)_2$—$N^+(CH_3)_3$ and the like.

Preferred $R^2$ groups are the $C_1$-$C_6$ alkyls, both substituted and unsubstituted, carboxy ($C_1$-$C_4$ alkyl), carbamoyl ($C_1$-$C_4$ alkyl), sulfo ($C_1$-$C_4$ alkyl), heteroaryl ($C_1$-$C_4$ alkyl) or cyano ($C_1$-$C_4$ alkyl).

Preferred substituents are CN, $CON(CH_3)_2$, $CONH_2$, $SOCH_3$, $SO_2CH_3$, $CO_2H$, $SO_3H$, $SO_2NH_2$ and

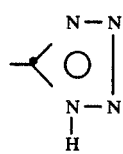

Examples of useful $R^3$ groups are hydrogen, $N(C_1$-$C_3 alkyl)$, $OC_1$-$C_4 alkyl$, $C_1$-$C_4 alkyl$, CN, $CF_3$, $CH_2OH$ and the like.

Preferred $R^3$ groups are H, —$CH_3$, —$OCH_3$, CN, —$SO_2CH_3$, $CH_2CN$, and the like.

Preferred $R^4$ and $R^5$ groups are where $R^4$ is hydrogen and $R^5$ is

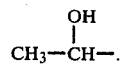

The

moiety is mono- or bicyclic quaternary heteroarylium group having 5-11 ring atoms of which, in addition to the quaternary $N^+$, up to four can be heteroatoms.

Representative

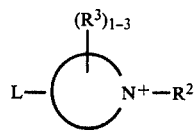

groups are:

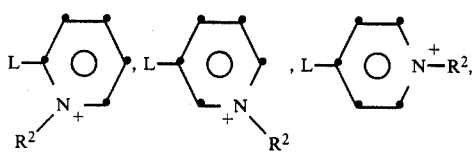

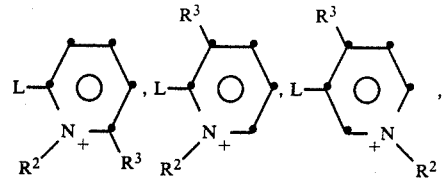

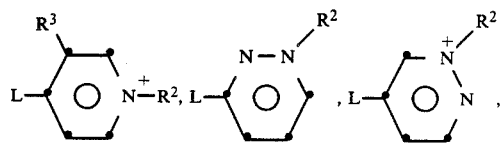

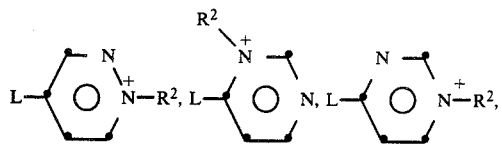

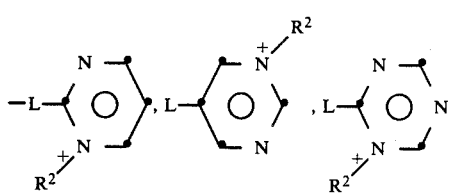

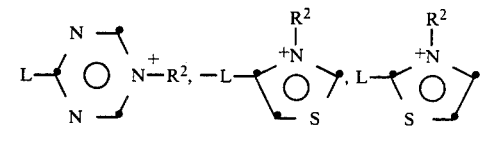

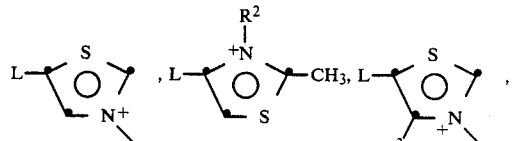

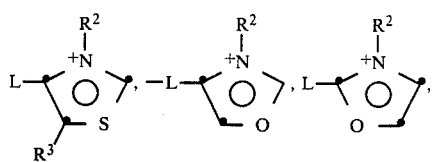

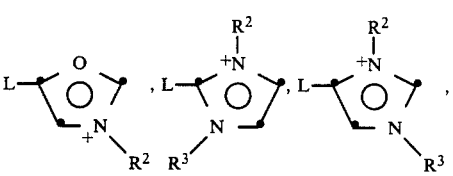

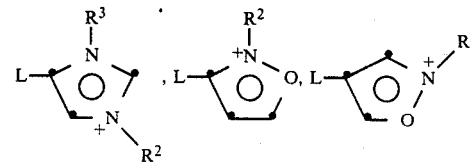

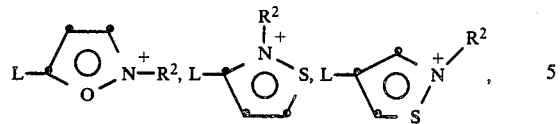
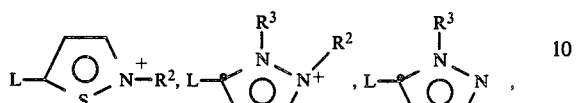
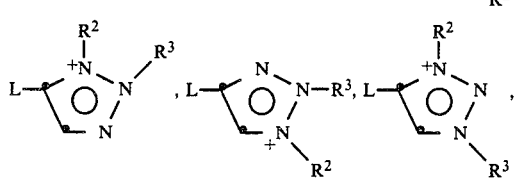
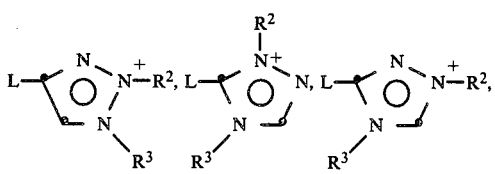
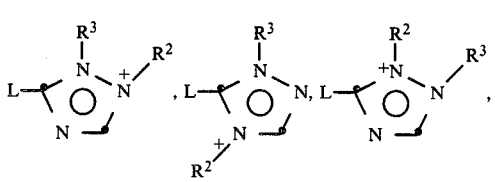
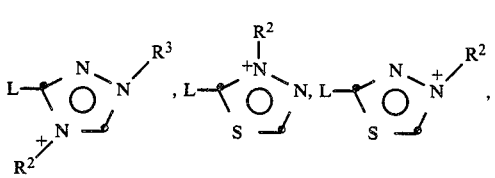
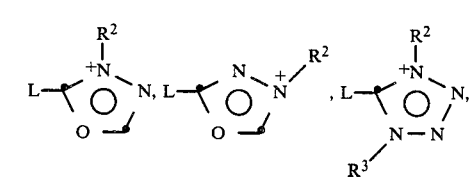
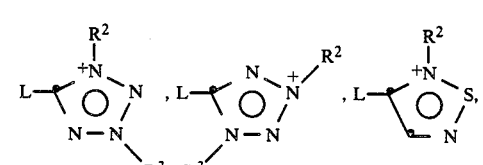
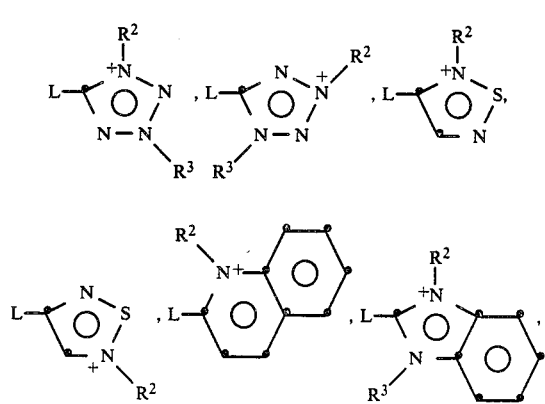

group is monocyclic heteroarylium having 5-6 ring atoms and optionally one heteroatom additional to the N atom already present, e.g., where $R^2$ and $R^3$ are as defined in the preferred list above and L is —CH$_2$— or —CH$_2$CH$_2$—.

An especially preferred subclass includes the nuclei shown above where $R^3$ (where present) is —CH$_3$, L is —CH$_2$— or —CH$_2$CH$_2$— and $R^2$ is C$_1$-C$_6$ alkyl, unsubstituted or substituted by —CN, —CON(CH$_3$)$_2$, —CONH$_2$, —SOCH$_3$, —SO$_2$CH$_3$, —CO$_2$H, —SO$_3$H, —SO$_2$NH$_2$ and

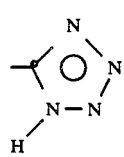

Further preferred compounds of Formula I include those where $R^1$ is H or CH$_3$ and

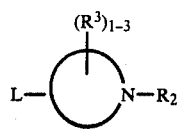

is

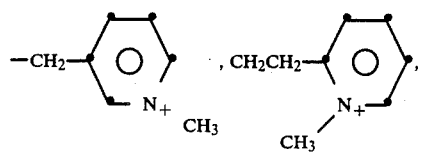

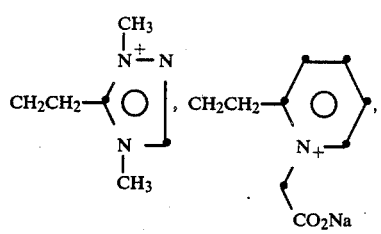

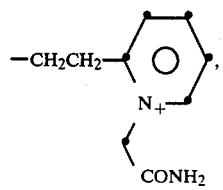

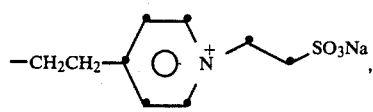

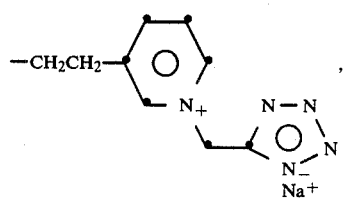

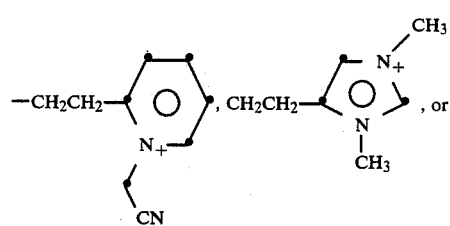

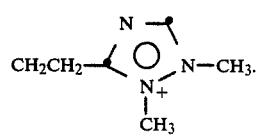

The compounds of Formula I include inner (Zwitterion) salts when Y is COO⁻ e.g.

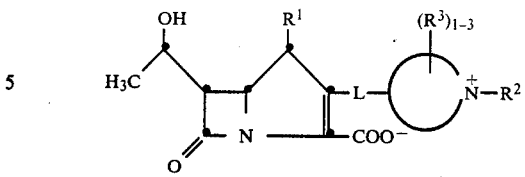

or, when Y is other than COO⁻, salts with an external, physiologically acceptable counterion Z⁻ such as Cl⁻, Br⁻, I⁻, OCH$_3$⁻, OSO$_2$CF$_3$⁻, OP(O) (O phenyl)$_2$⁻ and the like.

The inner salts are preferred.

Again, the compounds of Formula I include the stereoisomers as mixtures and as separate isomers.

A preferred isomer configuration is:

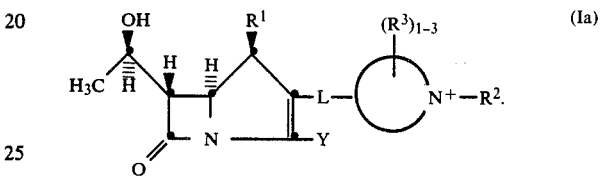

(Ia)

and where R$^1$ is CH$_3$, the preferred configuration is beta-CH$_3$.

The compounds of the present invention (I) are valuable antibiotics active against various Gram-positive and Gram-negative bacteria and accordingly find utility in human and veterinary medicine. Representative pathogens which are sensitive to antibiotics I include: *Staphylococcus aureus, Escherichia coli, Klebsiella pneumoniae, Bacillus subtilis, Salmonella typhosa, Pseudomonas* and *Bacterium proteus*. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The compounds of this invention may be used in any of a variety of pharmaceutical preparations. They may be employed in capsule, powder form, in liquid solution, or in suspension. They may be administered by a variety of means; those of principal interest include: topically or parenterally by injection (intravenously or intramuscularly).

Compositions for injection, a preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water. Topical applications may be formulated in hydrophobic or hydrophilic bases as ointments, creams, lotions, paints, or powders.

The dosage to be administered depends to a large extent upon the condition and size of the subject being treated as well as the route and frequency of administration—the parenteral route by injection being preferred for generalized infections. Such matters, however, are left to the routine discretion of the therapist according to principles of treatment well known in the antibiotic art. In general, a daily dosage consists of from about 5 to about 600 mg of active ingredient per kg of body weight of the subject in one or more treatments per day. A preferred daily dosage for adult humans lies in the range of from about 10 to 240 mg of active ingredient per kg of body weight. Another factor influencing the precise dosage regimen, apart from the nature of the infection and peculiar identity of the individual being treated, is the molecular weight of the chosen species of this invention (I).

The compositions for human delivery per unit dosage, whether liquid or solid, may contain from 0.1% to 99% of active material, the preferred range being from about 10–60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

The preferred method of administration of the formula I antibiotic is parenteral by i.v. infusion, i.v. bolus, or i.m. injection.

For adults, 5–50 mg of Formula I antibiotic per kg of body weight given 2, 3, or 4 times per day is preferred. Preferred dosage is 250 mg to 1000 mg of the Formula I antibiotic given two (b.i.d.) three (t.i.d.) or four (q.i.d.) times per day. More specifically, for mild infections, and particularly unitary tract infections, a dose of 250 mg t.i.d. or q.i.d. is recommended. For moderate infections against highly susceptible gram positive and gram negative organisms, a dose of 500 mg t.i.d. or q.i.d. is recommended. For severe, life-threatening infections against organisms at the upper limits of sensitivity to the antibiotic, a dose of 1000 t.i.d. or q.i.d. is recommended.

For children, a dose of 5–25 mg/kg of body weight given 2, 3, or 4 times per day is preferred; a dose of 10 mg/kg t.i.d. or q.i.d. is usually recommended.

Antibiotic compounds of Formula I are of the broad class known as carbapenems or 1-carbadethiapenems. Certain of these carbapenems are susceptible to attack by a renal enzyme known as dehydropeptidase (DHP). This attack or degradation may reduce the efficacy of the carbapenem antibiotic. Inhibitors of DHP and their use with carbapenem antibiotics are disclosed in the prior art [see published European Patent Applications No. 79102616.4 filed July 24, 1979 (Patent Number 10573); 79102615.6, filed July 24, 1979 (application no. 15573); and No. 82107174.3, filed Aug. 9, 1980 (application no. 72014)].

The present I compounds may, where DHP inhibition is desired or necessary, be combined or used with the appropriate DHP inhibitor as described in the aforesaid published applications. Thus, to the extent that the cited European patent applications 1.) define the procedure for determining DHP susceptibility of the present carbapenems and 2.) disclose suitable inhibitors, combination compositions and methods of treatment, they are incorporated herein by reference. A preferred weight ratio of I compound:DHP inhibitor in the combination compositions is about 1:1. A preferred DHP inhibitor is 7-(L-2-amino-2-carboxyethylthio)-2-(2,2-dimethylcyclopropanecarboxamide)-2-heptenoic acid or a useful salt thereof.

These combination compositions and their use is another embodiment of the present invention.

The compounds of Formula I may be prepared by any convenient process.

A key intermediate in the synthesis of compounds of Formula I, where the 6-position is substituted by 1-hydroxyethyl, is represented by general structures A and A'

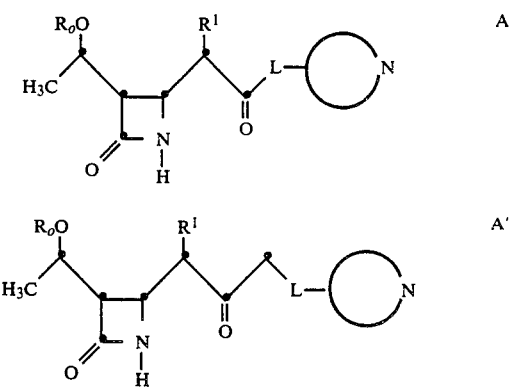

where $R_o$ is a hydroxyl protecting group such as t-butyldimethylsilyl, p-nitrobenzyloxycarbonyl, allyloxycarbonyl or the like, and $R^1$, L and

are as defined above. The synthesis of A and A' may be achieved by any convenient method, representative examples of which follow.

Method A-1

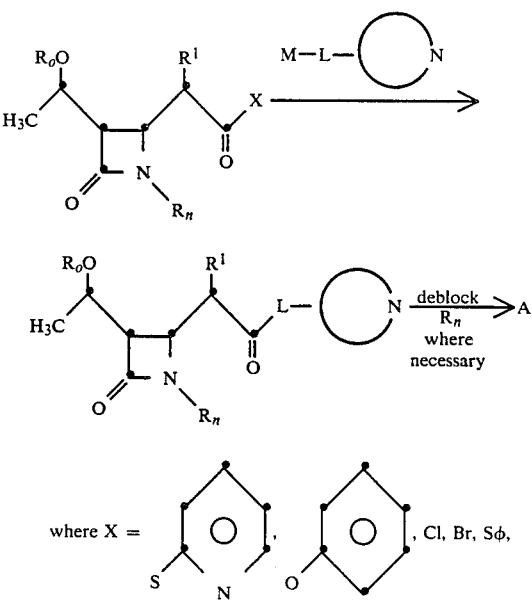

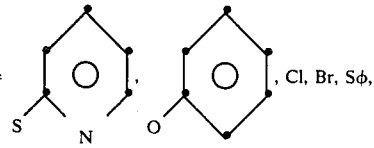

-continued
Method A-1

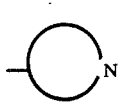

or the like;
M=Li, MgHalo, Cu or the like;
$R_n$=H or $(R)_3Si$, where R is $C_{1-4}$alkyl, such as $SiMe_3$ or $-Si(Me)_2t-Bu$; and
$R_o$, $R^1$, and

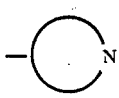

are as above.

Method A-2

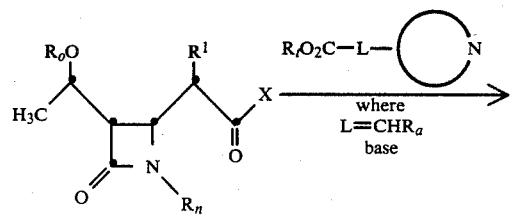

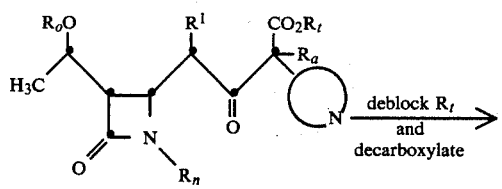

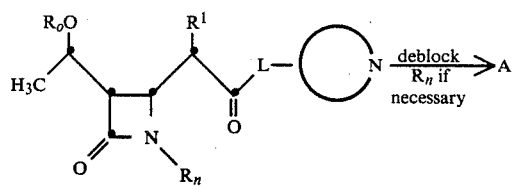

where
$R_t$=t—Bu, benzyl, allyl, p-nitrobenzyl, $(R)_3Si$, such as $Si(Me)_3$ or $SiMe_2$—t—Bu or the like;
$R_a$=H or $C_1$-$C_3$ alkyl; and
X, $R_o$, $R_n$, $R^1$, and

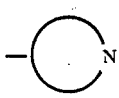

are as defined above.

Method A-3

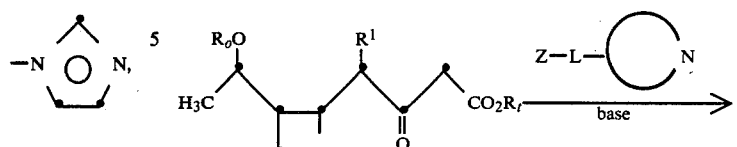

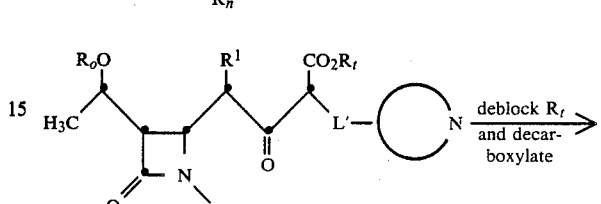

where
Z=X defined above, $OSO_2CH_3$, $OSO_2$—(-p—$C_6H_4$)$CH_3$, $OSO_2CF_3$ or the like; and
$R^1$, $R_o$, $R_n$, L, and

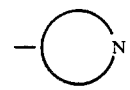

are as defined above.

Method A-4

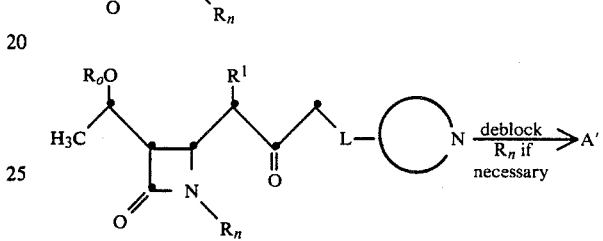

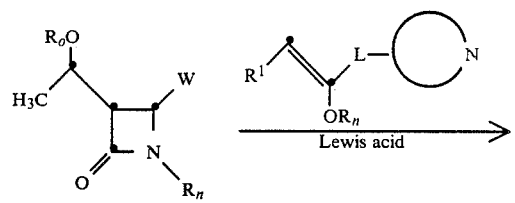

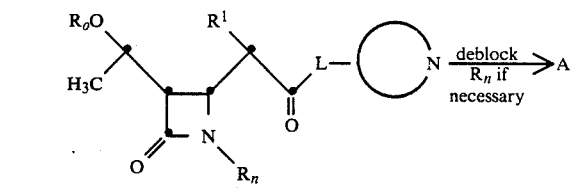

where
Lewis acid is $BF_3$ $O(CH_2CH_3)_2$, $AgBF_4$, TMSO-$SO_2CF_3$, $ZnI_2$ or the like;
W=X is defined above, —$OCOCH_3$, —$OCO\phi$, $SO_2\phi$ or the like; and
$R^1$, $R_o$, $R_n$, L and

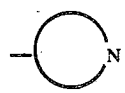

are as defined above.

Method A-5

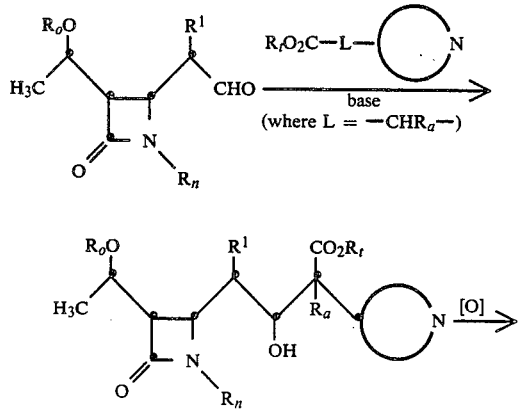

where $R^1$, $R_o$, $R_n$, L, M and

are as defined above.

Method A-6

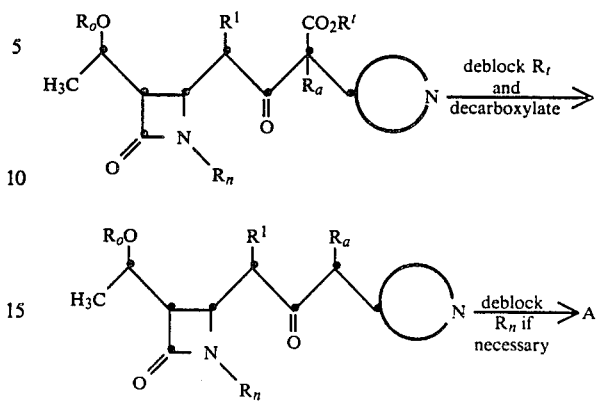

-continued
Method A-6

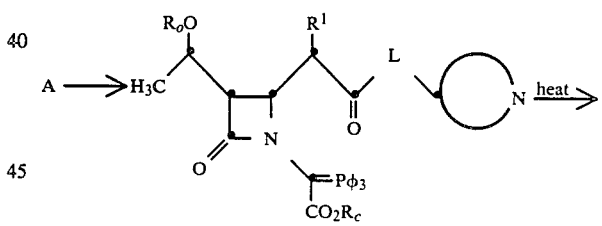

where
L is $-CHR_a$;
$R_a$ is hydrogen or $C_1-C_3$ alkyl; and
$R^1$, $R_o$, $R_n$, $R_t$ and

are as defined above.

Intermediates A and A' may be transformed to compounds of Formula I by any convenient process. Representative methods follow:

Method B-1

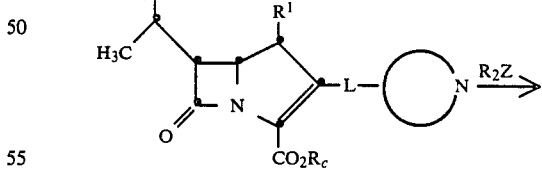

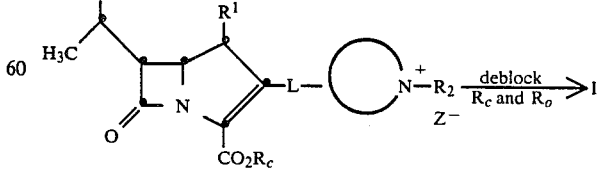

where
$R_c$ is p-nitrobenzyl, allyl or the like; and
$R^1$, $R_o$, $R_2$, Z, L and

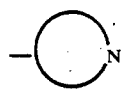

are as defined above.

Method B-2

A →

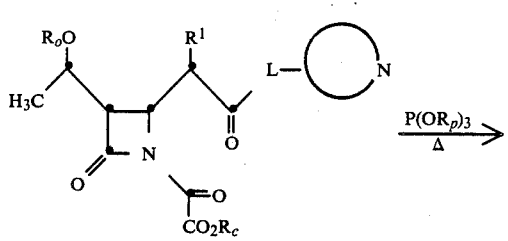

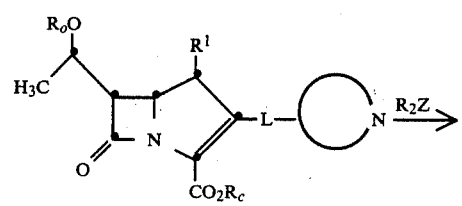

$\xrightarrow{\text{deprotect}}$ I
$R_o$ and $R_c$ where $R_p$ is —CH$_3$, —CH$_2$CH$_3$, —CH(CH$_3$)$_2$ or the like; and $R^1$, $R_2$, $R_c$, $R_o$, Z, L and

are as defined above.

In addition to the methods described above, many variations are possible involving permutation of the individual steps, for example:

Method C-1

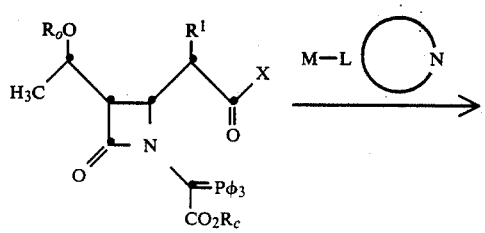

-continued
Method C-1

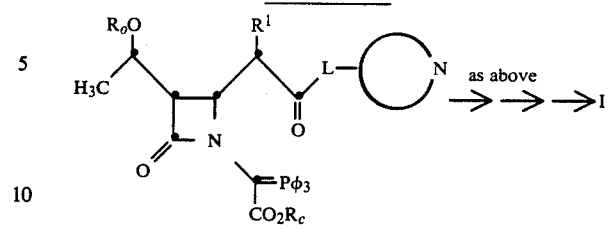

Method C-2

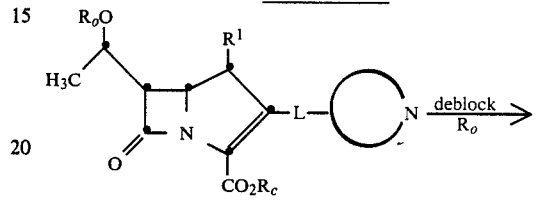

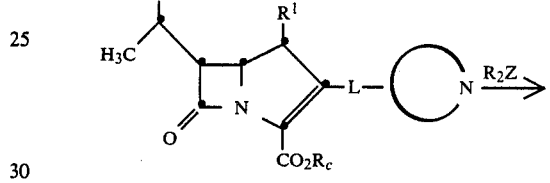

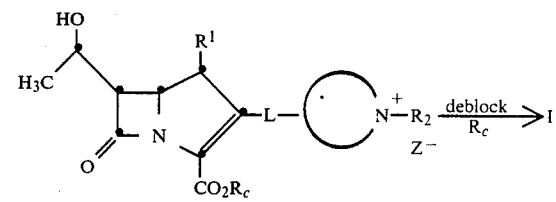

Method C-3

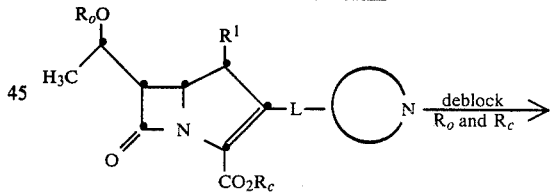

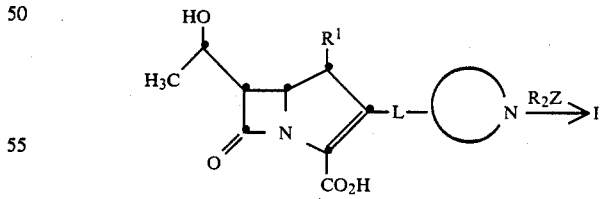

where $R^1$, $R_2$, $R_o$, $R_c$, M, Z, L and

are as defined above.

The following examples illustrate the preparation of compounds of Formula I where $R^1$ is methyl. The methods are equally applicable in the case where R¹ is hydrogen. The temperature is in degrees Celsius unless otherwise indicated. Where indicated, t-Bu is representative of tertiary butyl, and DMTB is representative of dimethyl-t-butyl-.

EXAMPLE 1

Preparation of 1R,5S,6S-6-(1R-hydroxyethyl)-1-methyl-2-(3-N-methylpyridiniummethyl)carbapen-2-em carboxylate (I)

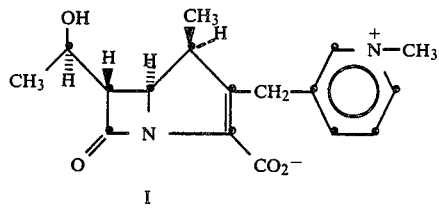

Step A:

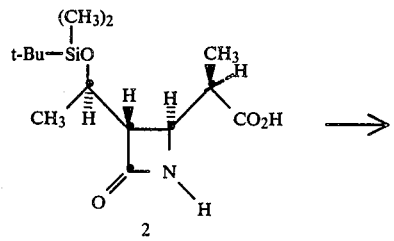

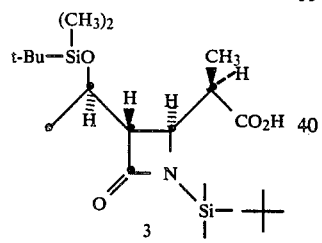

To a solution of acid 2 (7.00 g, 23.2 mmoles) in 112 dimethylformamide is added 22.8 ml (164 mmoles) of triethylamine followed by 17.50 g (116 mmoles) of t-butyldimethylsilylchloride. The mixture is stirred at room temperature for 2 hours and then the solvent is removed in vacuo. The residue is partitioned between 500 ml ethyl acetate and 100 ml water, the organic phase separated, dried over magnesium sulfate, filtered and concentrated to yield 13.00 g of crude trisilyl derivative. This material is dissolved in 240 ml of methanol and 24 ml of 30% aqueous acetic acid is added. The mixture is stirred at room temperature for 2 hours and then concentrated in vacuo to remove methanol. The residue is extracted with 250 ml of dichloromethane and the organic phase is washed with 50 ml of 0.1M pH 7 phosphate buffer. The dichloromethane solution is dried over magnesium sulfate, decolorized with activated charcoal and concentrated to a colorless oil which crystallized to yield 11.7 g 3.

Step B:

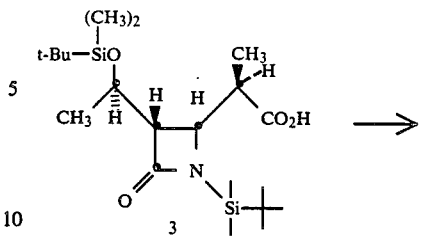

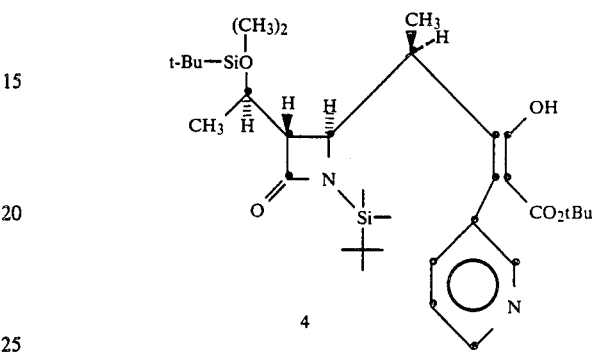

A heterogeneous mixture of 3 (4.14 g, 10 mmoles) and sodium carbonate (1.06 g, 10 mmoles) in 20 ml of tetrahydrofuran and 5 ml of acetonitrile is stirred at 50° for 2 hours then the solvent removed in vacuo. The residual sodium salt is suspended in 100 ml of dichloromethane, 0.02 ml of dimethylformamide added and the suspension cooled to −15° with stirring. Oxalyl chloride (0.96 ml, 11 mmoles) is added dropwise by syringe, causing vigorous gas evolution. The orange solution is maintained at −15° to allow the sodium chloride precipitate to settle. In a separate flask, t-butyl-3-pyridylacetate (1.737 g, 9.0 mmoles) is dissolved in 20 ml of tetrahydrofuran and cooled to −78°. A toluene solution of potassium hexamethyldisilazide (0.75M, 24 ml, 18 mmoles) is added dropwise with stirring and the resulting solution stirred 15 minutes at −78°. The acid chloride solution, prepared above, is then rapidly transferred by cannula to the solution of carbanion maintained at −78°. After 10 minutes at −78°, the reaction mixture is quenched with 100 ml of 10% aqueous potassium dihydrogen phosphate, diluted with 500 ml diethylether and stirred and allowed to come to room temperature. The ether layer is separated, washed with aqueous sodium bicarbonate and brine, dried over sodium sulfate and evaporated to yield 5.5 g of a crude product. Purification on silica gel with ethyl acetate-hexane as eluant affords 4.0 g of 4, used directly in the next step.

Step C:

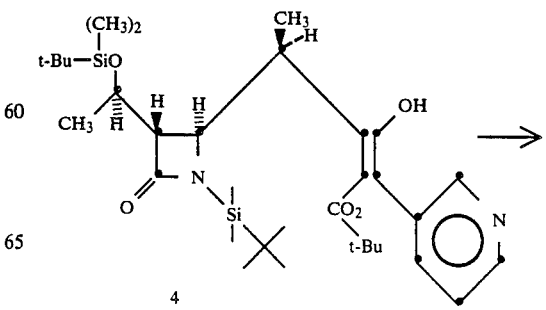

-continued

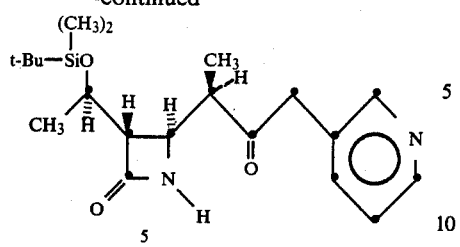
5

A solution of 4.0 g of 4 in 40 ml of dichloromethane is prepared and cooled to 0°. Trifluoroacetic acid (30 ml) is added dropwise with stirring and the resulting solution allowed to warm to room temperature. After 6 hours, 100 ml of toluene is added and the solvents removed in vacuo. Trituration of the resulting oil with ether affords 5 as a white solid, 2.5 g.

Step D:

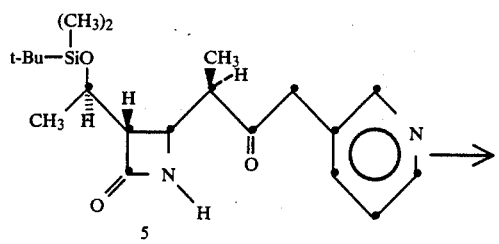
5

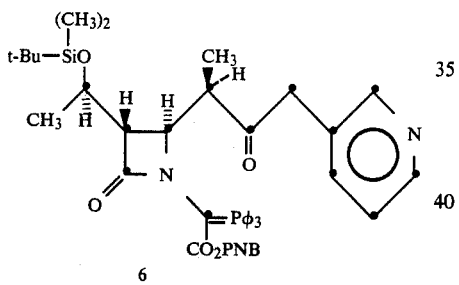
6

A mixture of 5 (2.5 g, 6.6 mmoles), p-nitrobenzyl glyoxalate hemihydrate (12.5 g, 6.6 mmoles) and 4.0 g powdered 3 Angstrom molecular sieves in 30 ml dry acetonitrile is stirred 5 hours at room temperature, then filtered and concentrated to a yellow glass. The crude hydroxy amide is dissolved in 50 ml of dichloromethane and 2,6-lutidine (0.777 g, 7.2 mmoles) is added. The solution is cooled to −20° and thionyl chloride (0.785 g, 6.6 mmoles) is added dropwise with stirring. After 30 minutes, a solution of triphenylphosphine (1.83 g, 7.0 mmoles) and 2.6-lutidine (0.77 g, 7.2 mmoles) in 10 ml dimethylformamide is added and the mixture allowed to warm to room temperature. The solution is concentrated to remove dichloromethane and the resulting dimethylformamide solution allowed to stand 5 hours at room temperature. The solvent is then removed in vacuo and the residue is partitioned between 100 ml ethyl acetate and 20 ml 10% aqueous sodium carbonate solution. The organic phase is dried over sodium sulfate and evaporated to yield 4.0 g phosphorane 6.

Step E:

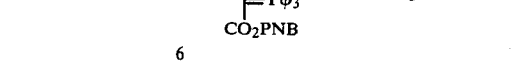
6

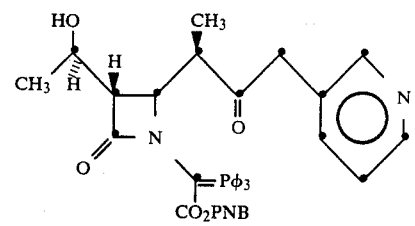
7

A solution of 6 (4.0 g, 4.8 mmoles) in 30 ml of tetrahydrofuran is cooled to 0° and 1.0 g of pyridinium(polyhydrogenfluoride) is added. The solution is stirred at 0° for 2 hours and then allowed to warm to room temperature. After 2 hours 1.0 ml of triethylamine is added and the mixture concentrated in vacuo. The residue is partitioned between 100 ml ethyl acetate and 20 ml saturated aqueous potassium bicarbonate and the organic phase is dried over sodium sulfate and evaporated to yield 3.5 g of 7.

Step F:

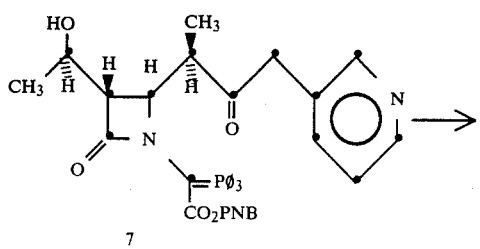
7

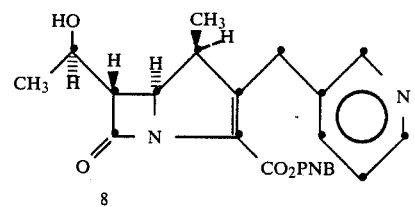
8

A solution of phosphorane 7 (3.0 g, 4.19 mmoles) in 100 ml dry toluene is degassed with argon and heated to 100° for 5 hours. The solution is then cooled to room temperature, concentrated in vacuo and the crude product purified by flash chromatography on silica gel to yield 1.1 g of carbapenem 8.

Step G:

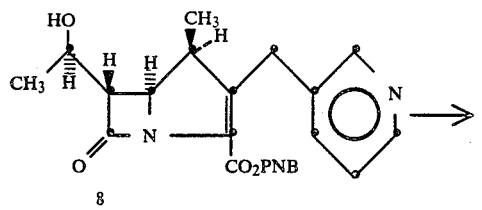

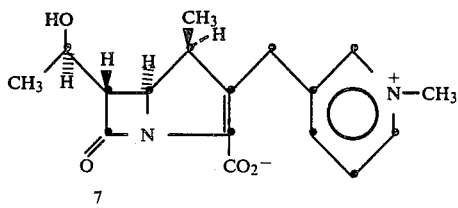

A solution of 8 (1.00 g, 2.28 mmoles) in 20 ml dichloromethane is cooled to 0° and methyl trifluoromethanesulfonate (0.377 g, 2.3 mmoles) is added dropwise with stirring. The mixture is stirred 2 hours during which time a gummy precipitate forms. The suspension is diluted with 50 ml dry ether and the supernatant removed by decantation. The residue is taken up in a mixture of 10 ml of N,N-dimethylacetamide, 40 ml of n-butanol 20 ml of ethyl acetate, 40 ml of water and 20 ml of 0.5M aqueous N-methylmorpholine hydrochloride (pH 6.8). Palladium hydroxide (20% carbon, 500 mg) is added and the mixture is hydrogenated at 50 psi for 75 minutes. The aqueous phase is then separated, filtered to remove catalyst, washed with 20 ml of ethyl acetate, concentrated to a volume of 10 ml and applied to a column of Dowex 50 (Na+). The desired product is eluted with water, active fractions are pooled and lyophilized to yield 250 mg of I.

EXAMPLE 2

Preparation of 1R,5S,6S-6-(1R-hydroxyethyl)-1-methyl-2-(2(2-N-methylpyridinium)ethyl)carbapen-2-em carboxylate (9)

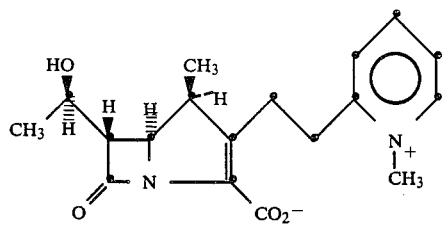

Step A:

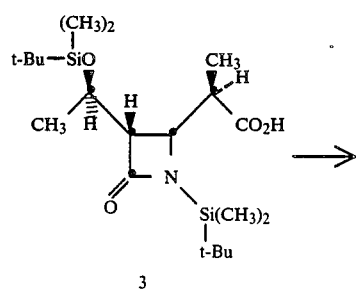

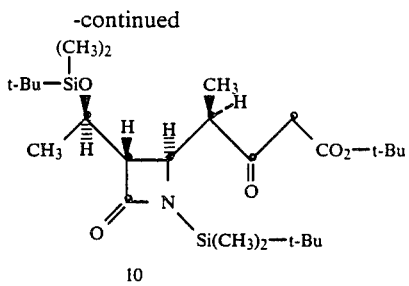

To a solution of 3 (4.14 g, 10 mmoles) in 20 ml tetrahydrofuran is added 1,1-carbonyldiimidazole (1.62 g, 10 mmoles). The mixture is stirred at room temperature for 2 hours, then magnesium bis(t-butylmalonate) salt (3.46 g, 10 mmoles) and 5 ml dimethylformamide are added and the mixture stirred at 50° for 24 hours. At the end of this period the reaction is quenched with 50 ml 10% aqueous potassium dihydrogen phosphate and extracted with 2×100 ml ethyl acetate. The combined organic phases are washed with brine, dried over sodium sulfate and evaporated to yield crude 10, which is purified by chromatography on silica gel to yield 4.0 g pure 10.

Step B:

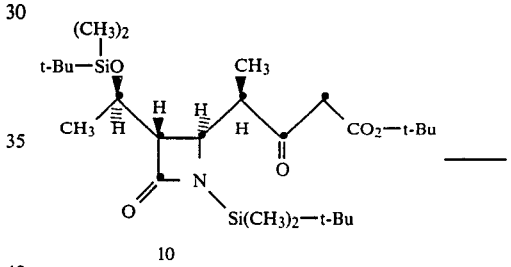

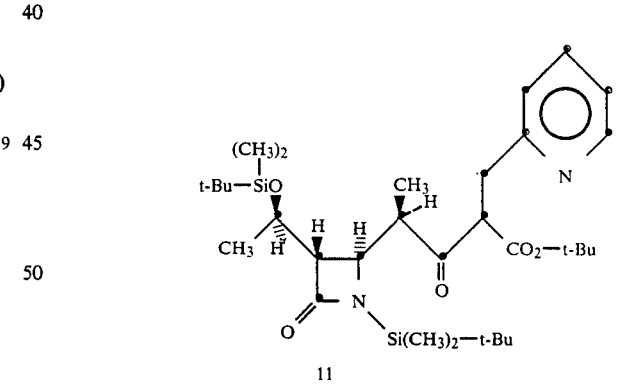

A solution of 10 (4.00 g, 8.0 mmoles) in 50 ml tetrahydrofuran is cooled to −78° and a solution of potassium hexamethyldisilazide (0.75M in toluene, 10.65 ml, 8.0 mmoles) is added. The solution is stirred 10 minutes at −78° then a solution of 2-chloromethylpyridine (1.02 g, 8.0 mmoles) in 10 ml dimethylformamide is added. The mixture is allowed to warm to room temperature over one hour, then stirred for 3 hours. Workup with 250 ml diethyl ether and 100 ml pH 7 phosphate buffer affords crude 11, 5.0 g, which is used directly in the next step.

Step C:

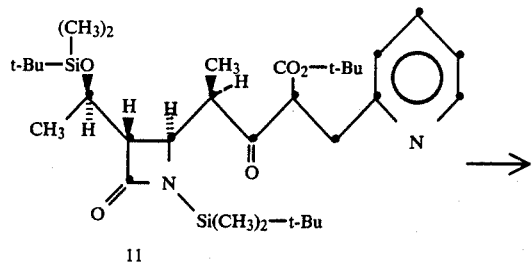

11

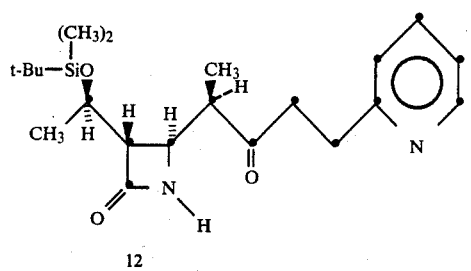

12

Crude 11 (5.0 g) is dissolved in 50 ml of dichloromethane and cooled to 0°. Trifluoroacetic acid (50 ml) is added dropwise with stirring and the mixture is then allowed to warm to room temperature. After 6 hours at room temperature the mixture is diluted with 100 ml of toluene and concentrated in vacuo. Pure ketone 12 (3.1 g) is obtained by chromatography on silica gel.

Steps D–G:

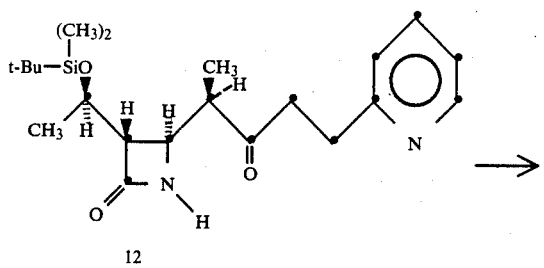

12

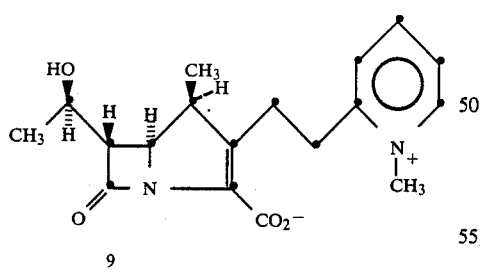

9

The transformation of 12 to 9 follows in a manner exactly analogous to that described in Steps D–G in Example 1.

EXAMPLE 3

Utilizing the procedures of Examples 1–2, the following compounds listed in Table I are prepared, wherein $R^1$ for each compound can be methyl or hydrogen. Remarks relative to the procedures are presented in the footnotes to Table I.

TABLE I

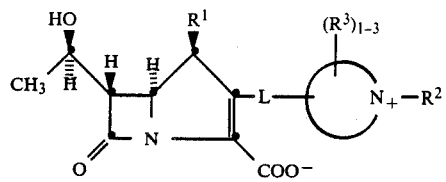

| Compound | L | $-\bigcirc\!\!\!\!N$ | $R^2$ |
|---|---|---|---|
| 1. | $CH_2$ | 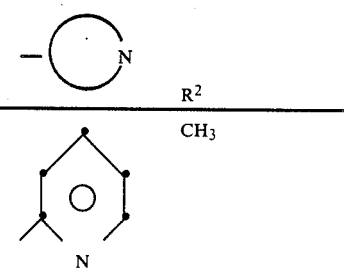 | $CH_3$ |
| 2. | CH\|CH_3 | " | " |
| 3. | $CH_2CH_2$ | " | " |
| 4. | $CH_2CH_2CH_2$ | " | " |
| 5. | $CH_2CH_2$ | " | $CH_2CH_3$ |
| 6. | " | " | $CH_2CO_2H$ |
| 7. | " | " | $CH_2CONH_2$ |
| 8. | " | " | 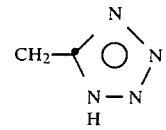 |
| 9. | " | " | $CH_2SOCH_3$ |
| 10. | " | 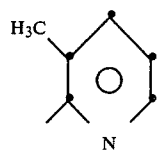 | $CH_3$ |
| 11. | " | 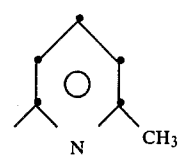 | " |
| 12. | CHCH_2\|CH_3 | 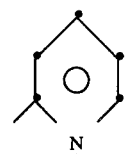 | " |
| 13. | $CH_2CH$\|$CH_3$ | 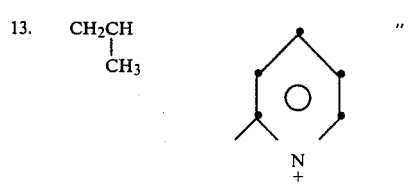 | " |

TABLE I-continued

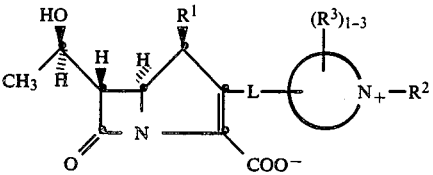

| Compound | L | ⌬N (ring) | R² |
|---|---|---|---|
| 14. | CH₂ | 4-methylpyridinium | " |
| 15. | " | " | CH₂CH₃ |
| 16. | " | " | CH₂CO₂H |
| 17. | " | " | CH₂CONH₂ |
| 18. | " | " | CH₂-(tetrazole-NH) |
| 19. | " | " | CH₂SOCH₃ |
| 20. | CH₂CH₂ | " | CH₃ |
| 21. | " | " | CH₂CO₂H |
| 22. | " | " | CH₂CONH₂ |
| 23. | CH₂ | " | CH₂-(tetrazole-NH) |
| 24. | CH(CH₃) | " | CH₃ |
| 25. | " | " | CH₂CH₃ |
| 26. | CH₂CH₂CH₂ | " | CH₃ |
| 27. | CH₂ | 3-methylpyridinium | CH₃ |
| 28. | " | " | CH₂CH₃ |
| 29. | " | " | CH₂CO₂H |
| 30. | " | " | CH₂CONH₂ |
| 31. | " | " | CH₂-(tetrazole-NH) |
| 32. | " | " | CH₂SOCH₃ |
| 33. | CH₂CH₂ | " | CH₂CO₂H |
| 34. | " | " | CH₂CONH₂ |
| 35. | " | " | CH₂-(tetrazole-NH) |
| 36. | " | " | CH₂SOCH₃ |
| 37. | CH(CH₃) | " | CH₃ |
| 38. | CH₂CH₂CH₂ | " | " |
| 39. | CH₂ | 2-methylpyridinium | " |
| 40. | " | thiazolium | " |
| 41. | " | " | CH₂CH₃ |
| 42. | CH₂CH₂ | " | CH₃ |
| 43. | CH₂ | 4-methylthiazolium | " |
| 44. | CH₂CH₂ | " | " |
| 45. | " | 5-methylthiazolium | " |
| 46. | " | thiazolium | " |
| 47. | " | oxazolium | " |
| 48. | " | " | " |

TABLE I-continued

Structure (compounds 49–66): bicyclic β-lactam core with HO-CH(CH₃)-, R¹, COO⁻, L-linked heterocyclic ammonium group (R³)₁₋₃, N⁺-R²

Key: —◯N represents the heterocyclic ring attachment

| Compound | L | Ring | R² |
|---|---|---|---|
| 49. | " | oxadiazolium (N⁺, O) | " |
| 50. | " | N-CH₃ imidazole with N⁺ | " |
| 51. | " | +N, O ring with N-CH₃ | " |
| 52. | " | CH₃-N, triazolium N⁺ | " |
| 53. | " | CH₃-N, N⁺, N triazolium | " |
| 54. | " | N, N⁺ with N-CH₃ | " |
| 55. | " | +N, N with N-CH₃ | " |
| 56. | " | N, +N, S thiadiazolium | " |
| 57. | " | N⁺, N, S thiadiazolium | " |
| 58. | " | N⁺, N, O | " |
| 59. | " | +N, N, O | " |
| 60. | " | tetrazolium with N-CH₃ | " |
| 61. | " | N, N, N⁺ tetrazolium | " |
| 62. | " | +N, N, N with N-CH₃ | " |
| 63. | " | pyrrolium N⁺ | " |
| 64. | " | N⁺ ring | " |
| 65. | " | S, N⁺ thiazolium | " |
| 66. | " | S, N⁺ thiazolium | " |

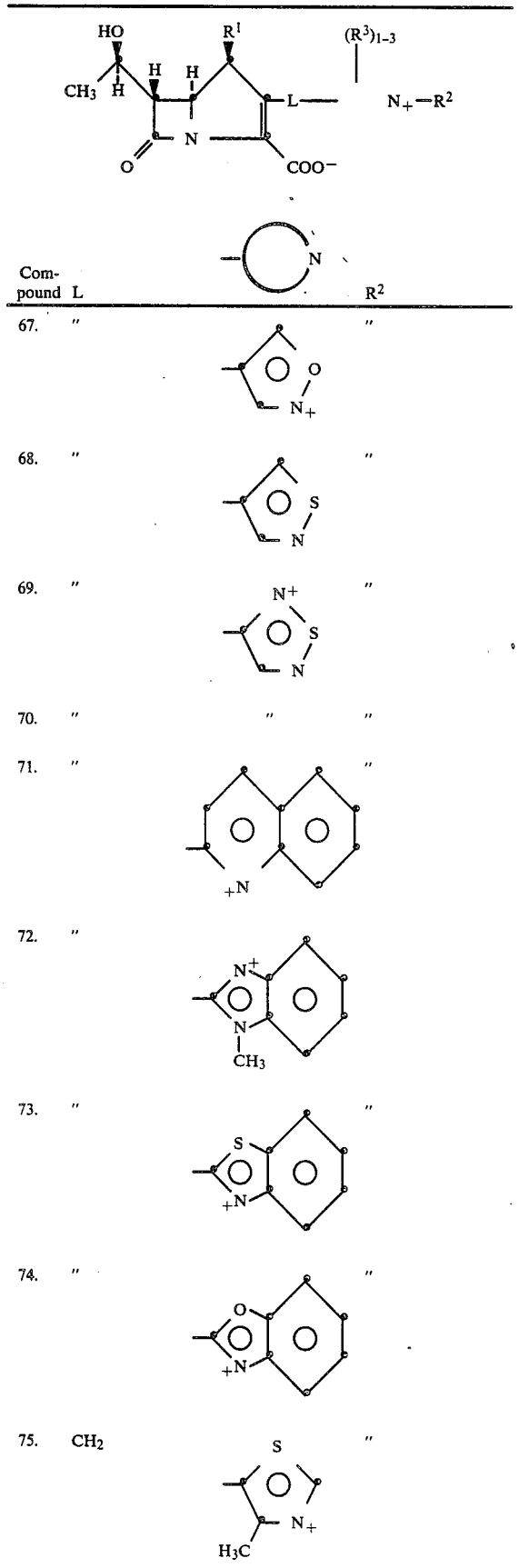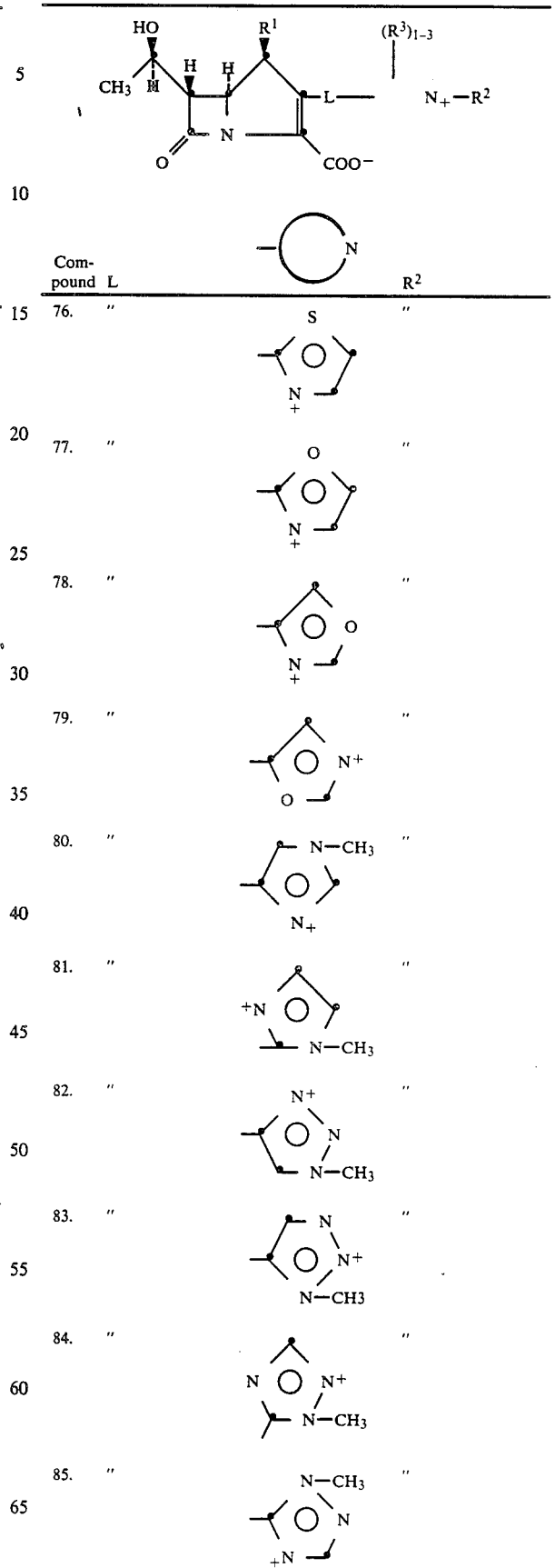

TABLE I-continued

| Compound | L | (ring structure) | R² |
|---|---|---|---|
| 86. | " | N+/O/S ring with N | " |
| 87. | " | N+/N/O/S ring | " |
| 88. | " | N/O/N+/O ring | " |
| 89. | " | N+/N/O/O ring | " |
| 90. | " | N–N/O/N(CH₃) triazole | " |
| 91. | " | N/N/O/N–CH₃/N+ ring | " |
| 92. | " | +N/N/N/O/N(CH₃) tetrazole | " |
| 93. | " | O/N+ ring | " |
| 94. | " | " | " |
| 95. | " | S/N+ ring | " |
| 96. | " | " | " |
| 97. | " | O/N+ ring | " |
| 98. | " | S/N+ ring | " |
| 99. | " | N/O/S/N+ ring | " |
| 100. | " | bicyclic (naphthyridinium, +N) | " |
| 101. | " | benzimidazolium N+/N–CH₃ | " |
| 102. | " | benzothiazolium S/N+ | " |
| 103. | " | benzoxazole O/N | " |
| 104. | " | pyridinium N+ | CH₂CN |
| 105. | CH₂CH₂ | " | CH₂CN |
| 106. | CH₃–CHCH₂ | " | CH₃ |

TABLE I-continued

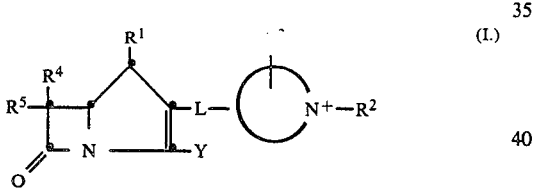

| Compound | L | R² |
|---|---|---|
| 107. | " | " |
| 108. | CH₂ | " CH₂CN |
| 109. | CH₂CH₂ | " " |
| 110. | " | " |
| 111. | CH₂ | " " |

What is claimed is:

1. A compound having the formula:

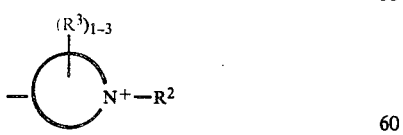

wherein:

$R^1$ is hydrogen or methyl;

$R^4$ and $R^5$ are independently H, CH₃—, CH₃CH₂—, (CH₃)₂CH—, HOCH₂—, CH₃CH(OH)—, (CH₃)₂C(OH)—, FCH₂—, F₂CH—, F₃C—, CH₃CH(F)—, (CH₃)₂C(F)—; CH₃CF₂—, or L is a bridging group comprising substituted or unsubstituted $C_1$-$C_4$ straight, $C_2$-$C_6$ branched or $C_3$-$C_7$ cycloalkyl groups wherein the substituents are selected from $C_1$-$C_6$ alkyl, O-$C_1$-$C_6$ alkyl, S-$C_1$-$C_6$ alkyl, CF₃, N($C_1$-$C_6$ alkyl)₂;

is a mono- or bicyclic heteroarylium group containing from 5-11 ring atoms of which up to 5 are heteroatoms in addition to the quaternary nitrogen;

wherein:

$R^2$ is (1) an unsubstituted or substituted $C_1$-$C_6$ alkyl radical;

(2) an unsubstituted or substituted $C_2$-$C_6$ alkenyl radical;

(3) an unsubstituted or substituted $C_2$-$C_6$ alkynyl radical;

(4) a $C_3$-$C_7$ cycloalkyl radical in which the ring is substituted or unsubstituted and one or more atoms may be replaced by a heteroatom;

(5) a $C_3$-$C_7$ cycloalkyl methyl radical in which the ring may be substituted and one or more atoms may be replaced by a heteroatom;

(6) an unsubstituted or substituted $C_5$-$C_7$ cycloalkenyl radical;

(7) an unsubstituted or substituted bivalent $C_2$-$C_6$ alkylidene radical, optionally interrupted by a heteroatom, and joined to the heteroarylium group to form a ring which is carbocyclic or in which one or more atoms is replaced by a heteroatom and wherein the new ring may contain one or more double bonds;

(8) an unsubstituted or substituted phenyl or heteroaryl radical;

(9) an unsubstituted or substituted phenyl ($C_1$-$C_4$ alkyl) or heteroaryl ($C_1$-$C_4$ alkyl) radical;

(10) a cyano ($C_1$-$C_4$ alkyl) radical;

(11) a carboxy ($C_1$-$C_4$ alkyl) radical;

(12) a sulfo ($C_1$-$C_4$ alkyl) radical;

(13) a carbamoyl ($C_1$-$C_4$ alkyl) radical;

(14) a phosphonyl ($C_1$-$C_4$ alkyl) radical;

(15) a hydroxy ($C_1$-$C_4$ alkyl) radical; or

(16) an amino ($C_1$-$C_4$ alkyl) radical in which the nitrogen atom is unsubstituted or substituted with one to three $C_1$-$C_4$ alkyl groups;

wherein the substituents in the above definitions of $R^2$ are independently selected from the group consisting of:

(a) a trifluoromethyl group;

(b) a halogen atom;

(c) an unsubstituted or substituted $C_1$-$C_4$ alkoxyl radical;

(d) a hydroxy group;

(e) an unsubstituted or substituted ($C_1$-$C_6$ alkyl) carbonyloxy radical;

(f) a carbamoyloxy radical which is unsubstituted or substituted on nitrogen with one or two $C_1$-$C_4$ alkyl groups;

(g) a $C_1$-$C_6$ alkylthio radical, $C_1$-$C_6$ alkylsulfinyl radical or $C_1$-$C_6$ alkylsulfonyl radical, each of which is unsubstituted or substituted on the alkyl group;

(h) a sulfo group;

(i) a sulfamoyl group which is unsubstituted or substituted on nitrogen by one or two $C_1$-$C_4$ alkyl groups;

(j) a formylamino group;

(k) an unsubstituted or substituted ($C_1$-$C_6$ alkyl)-carbonylamino radical;

(l) a ($C_1$-$C_4$ alkoxyl) carbonylamino radical;

(m) a ureido group in which the terminal nitrogen is unsubstituted or substituted with one or two $C_1$-$C_4$ alkyl groups;

(n) an arylsulfonamido or a ($C_1$-$C_6$ alkyl)sulfonamido group;

(o) a cyano group;

(p) a formyl or acetalized formyl radical;

(q) an unsubstituted or substituted ($C_1$–$C_6$ alkyl)-carbonyl radical wherein the carbonyl is free or acetalized;

(r) an unsubstituted or substituted phenylcarbonyl or heteroarylcarbonyl radical;

(s) a carboxyl group;

(t) a ($C_1$–$C_6$ alkoxy)carbonyl radical;

(u) a carbamoyl radical which is unsubstituted or substituted on nitrogen by one or two $C_1$–$C_4$ alkyl groups;

(v) an N-hydroxycarbamoyl or N($C_1$–$C_4$ alkoxy)-carbamoyl radical in which the nitrogen atom may be additionally substituted by a $C_1$–$C_4$ alkyl group;

(w) a thiocarbamoyl group;

(x) a 5-(1H)-tetrazolyl group;

(y) a phosphonate group —P(O)(OH)OR' where R' is $C_1$–$C_3$ alkyl;

(z) an alkyl phosphonate group —$(CH_2)_n$P(O)(OH)(OR') where n=1 to 3 and R' is $C_1$–$C_3$ alkyl;

(aa) hydrogen;

(ab) an unsubstituted or substituted $C_1$–$C_6$ alkyl radical;

(ac) an unsubstituted or substituted $C_2$–$C_6$ alkenyl radical;

(ad) an unsubstituted or substituted $C_2$–$C_6$ alkynyl radical;

(ae) a $C_3$–$C_7$ cycloalkyl radical in which the ring is substituted or unsubstituted and one or more atoms may be replaced by a heteroatom;

(af) a $C_3$–$C_7$ cycloalkyl methyl radical in which the ring may be substituted and one or more atoms may be replaced by a heteroatom;

(ag) an unsubstituted or substituted $C_5$–$C_7$ cycloalkenyl radical;

(ah) an unsubstituted or substituted phenyl or heteroaryl radical; and (ai) an unsubstituted or substituted phenyl ($C_1$–$C_4$ alkyl) or heteroaryl ($C_1$–$C_4$ alkyl) radical; and $R^3$ is (a) hydrogen;

(b) an unsubstituted or substituted $C_1$–$C_6$ alkyl radical;

(c) an unsubstituted or substituted $C_2$–$C_6$ alkenyl radical;

(d) an unsubstituted or substituted $C_2$–$C_6$ alkynyl radical;

(e) a $C_3$–$C_7$ cycloalkyl radical in which the ring is substituted or unsubstituted and one or more atoms may be replaced by a heteroatom;

(f) a $C_3$–$C_7$ cycloalkyl methyl radical in which the ring may be substituted and one or more atoms may be replaced by a heteroatom;

(g) an unsubstituted or substituted $C_5$–$C_7$ cycloalkenyl radical;

(h) an unsubstituted or substituted phenyl or heteroaryl radical;

(i) an unsubstituted or substituted phenyl ($C_1$–$C_4$ alkyl) or heteroaryl ($C_1$–$C_4$ alkyl) radical; and (j) a trifluoromethyl group;

(k) a halogen atom;

(l) an unsubstituted or substituted $C_1$–$C_4$ alkoxyl radical;

(m) a $C_1$–$C_6$ alkylthio radical, $C_1$–$C_6$ alkylsulfinyl radical or $C_1$–$C_6$ alkylsulfonyl radical, each of which is unsubstituted or substituted on the alkyl group;

(n) a mono ($C_1$–$C_4$ alkyl) amino or di($C_1$–$C_4$ alkyl)amino group, each of which is unsubstituted or substituted on the alkyl group; or (o) a cyano group; and Y is (i) COOH or a pharmaceutically acceptable ester or salt thereof, (ii) COOR wherein R is a removable carboxy protecting group, (iii) COOM wherein M is an alkali metal, or (iv) $COO^-$; provided that when Y is other than (iv) a counterion $Z^-$ is provided.

2. A compound of claim 1 wherein $R^1$ is $CH_3$.

3. A compound of claim 1 wherein L is substituted or unsubstituted branched or linear $C_1$–$C_4$ alkyl.

4. A compound of claim 3 wherein L is —$CH_2$—, —$CH(CH_3)$—, —$(CH_2)_2$—, or —$CH(CH_3)CH_2$—.

5. A compound of claim 1 wherein

is monocyclic heteroarylium having 5–6 ring atoms.

6. A compound of claim 5 wherein

is a pyridinium, diazolium, triazolium, thiazolium or oxazolium group.

7. A compound of claim 1 wherein $R^2$ is an unsubstituted or substituted $C_1$–$C_6$ alkyl group, carboxy ($C_1$–$C_4$ alkyl), carbamoyl ($C_1$–$C_4$ alkyl), sulfo ($C_1$–$C_4$ alkyl), heteroaryl ($C_1$–$C_4$ alkyl), or cyano ($C_1$–$C_4$ alkyl).

8. A compound of claim 1 wherein $R^3$ is hydrogen, N($C_1$–$C_3$ alkyl), O-$C_1$–$C_4$ alkyl, $C_1$–$C_4$ alkyl, CN, $CF_3$ or $CH_2OH$.

9. A compound of claim 1 wherein the compound is a member selected from the group wherein $R^1$ is H and

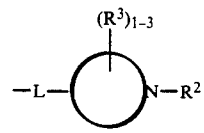

is selected from

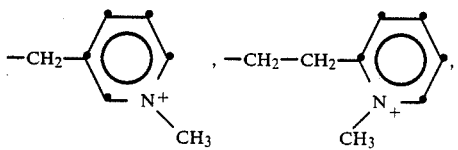

-continued
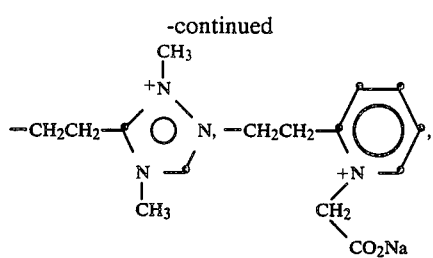
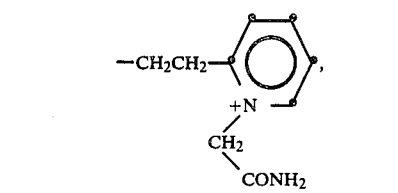
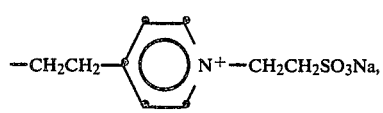
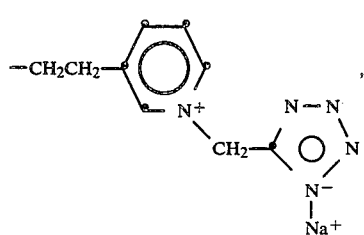
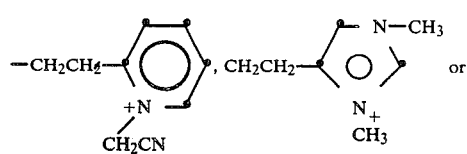
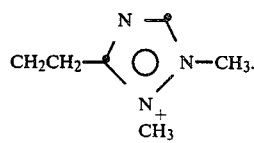
-continued
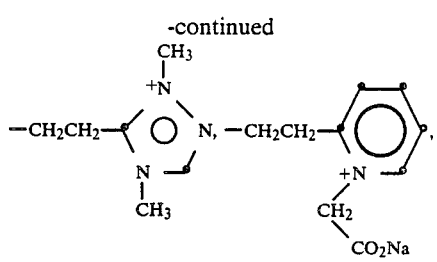
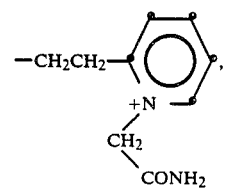
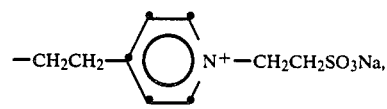
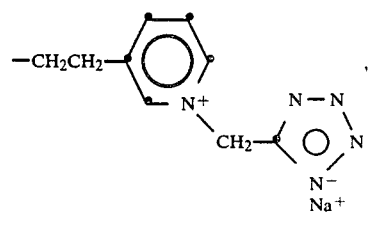
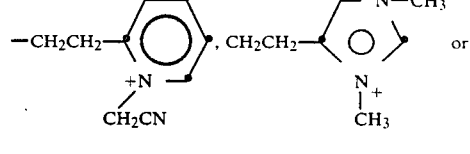
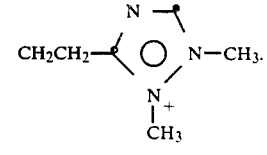
10. A compound of claim 1 wherein the compound is a member selected from the group wherein $R^1$ is $CH_3$ and
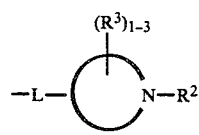
is selected from
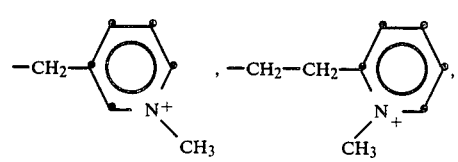
11. A compound of claim 1 having the stereochemical configuration:
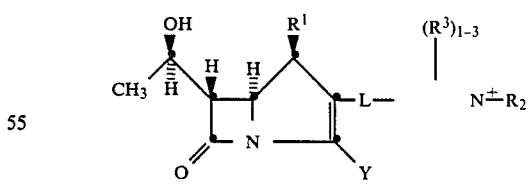
12. The compound of claim 11 having the structure:
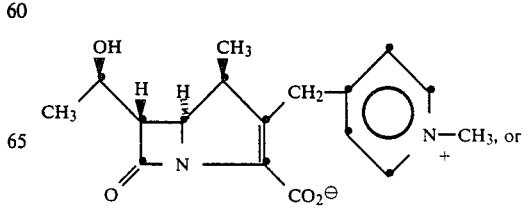

-continued

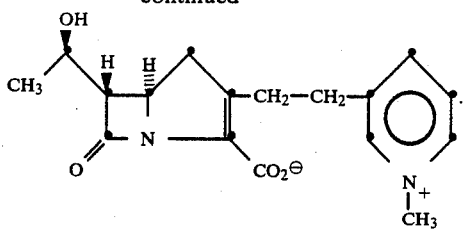

13. A compound of claim 11 wherein $R^1$ is $CH_3$, having a beta configuration.

14. The combination of a compound of claim 1 and a DHP inhibitor.

15. A combination of claim 14 wherein the DHP inhibitor is 7-(L-2-amino-2-carboxyethylthio)-2-(2,2-dimethylcyclopropanecarboxamido)-2-heptenoic acid.

16. A pharmaceutical composition for antibiotic use comprising an antibacterially effective amount of a compound of claim 1 and, optionally, a pharmaceutically acceptable carrier.

17. A pharmaceutical composition for antibiotic use comprising an antibacterially effective amount of a compound of claim 1, an inhibitorily effective amount of a DHP inhibitor, and, optionally, a pharmaceutically acceptable carrier.

18. A pharmaceutical composition according to claim 17 wherein the DHP inhibitor is 7-(L-2-amino-2-carboxyethylthio)-2-(2,2-dimethylcyclopropanecarboxamido)-2-heptenoic acid.

19. A method of treating bacterial infections in human or animal subjects in need of such treatment comprising coadministering to said subjects an antibacterially effective amount of a compound of claim 1, an inhibitorily effective amount of a DHP inhibitor.

20. A method according to claim 19 wherein the DHP inhibitor is 7-(L-2-amino-2-carboxyethylthio)-2-(2,2-dimethylcyclopropanecarboxamido)-2-heptenoic acid.

21. A method of treating bacterial infections in human or animal subjects in need of such treatment comprising administering to said subjects an antibacterially effective amount of a compound of claim 1.

* * * * *